(12) United States Patent
Blizzard et al.

(10) Patent No.: US 6,251,890 B1
(45) Date of Patent: Jun. 26, 2001

(54) CARBAPENEM ANTIBACTERIAL COMPOUNDS, COMPOSITIONS CONTAINING SUCH COMPOUNDS AND METHODS OF TREATMENT

(75) Inventors: Timothy A. Blizzard, Rahway; Ronald W. Ratcliffe, Matawan; Jerry D. Morgan, II, Piscataway; Robert R. Wilkening, Maplewood, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/524,355

(22) Filed: Mar. 13, 2000

Related U.S. Application Data

(63) Continuation of application No. 09/133,116, filed on Aug. 12, 1998, now abandoned.
(60) Provisional application No. 60/055,273, filed on Aug. 13, 1997.

(51) Int. Cl.[7] ...................... C07D 477/14; C07D 516/06; A61P 31/04; A61K 31/4747; A61K 31/4743
(52) U.S. Cl. .................... 514/210.09; 540/302; 540/543; 544/71; 544/231; 546/17; 546/18; 546/64; 548/208
(58) Field of Search ........................ 540/302; 514/210.09

(56) References Cited

U.S. PATENT DOCUMENTS

| | | | |
|---|---|---|---|
| 4,309,438 | 1/1982 | Christensen et al. | 424/274 |
| 4,479,947 | 10/1984 | Christensen et al. | 424/203 |
| 5,756,725 | 5/1998 | Wilkening et al. | 540/302 |

OTHER PUBLICATIONS

S. M. Schmitt et al., *J. Antibiotics*, 41(6), pp. 780–787 (1988).

*Primary Examiner*—Mark L. Berch
(74) *Attorney, Agent, or Firm*—Sylvia A. Ayler; Mark R. Daniel

(57) ABSTRACT

The present invention relates to carbapenem antibacterial agents of formula I:

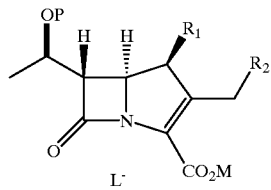

or a pharmaceutically acceptable salt thereof, wherein: $R^2$ represents:

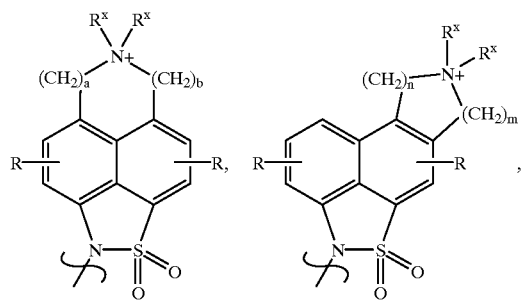

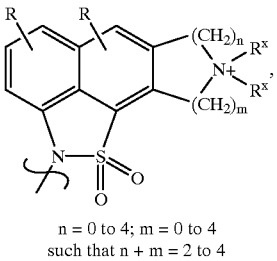

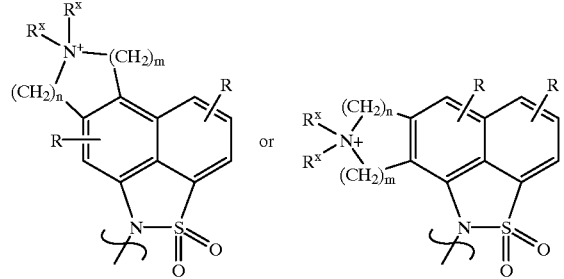

in formula I, in which the carbapenem nucleus is substituted at the 2-position with a naphthosultam linked through a $CH_2$ group. The naphthosultam is further substituted with various substituent groups including at least one cationic group.

23 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional Application No. 60/055,273, filed Aug. 13, 1997. This is a continuation of application Ser. No. 09/133,116 abandoned, filed Aug. 12, 1998.

BACKGROUND OF THE INVENTION

The present invention relates to carbapenem antibacterial agents in which the carbapenem nucleus is substituted at the 2-position with a naphthosultam linked through a $CH_2$ group. The naphthosultam is further substituted with various substituent groups including at least one cationic group.

The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The compounds of the invention are represented by formula I:

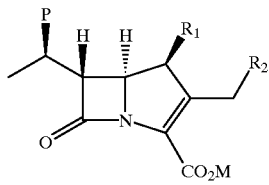

I or a pharmaceutically acceptable salt thereof, wherein:
$CO_2M$ represents a carboxylic acid, a carboxylate anion, a pharmaceutically acceptable ester group or a carboxylic acid protected by a protecting group;
$R^1$ represents H or methyl;
P represents hydrogen, hydroxyl, F or hydroxyl protected by a hydroxyl-protecting group;
$R^2$ represents:

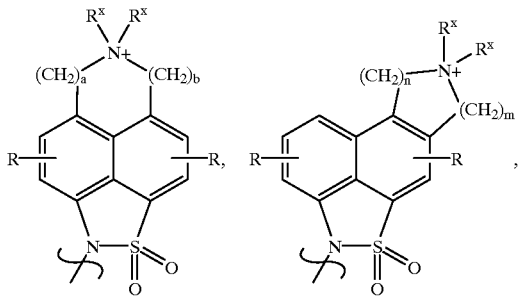

a = 0 to 3; b = 0 to 3
such that a + b = 1 to 3 n = 0 to 4; m = 0 to 4
such that n + m = 2 to 4

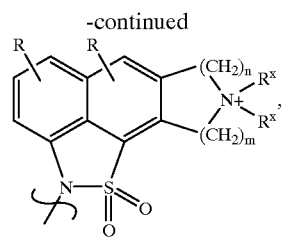

n = 0 to 4; m = 0 to 4
such that n + m = 2 to 4

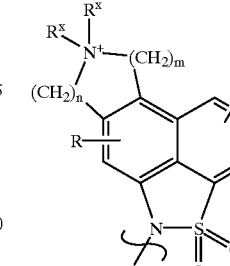 or 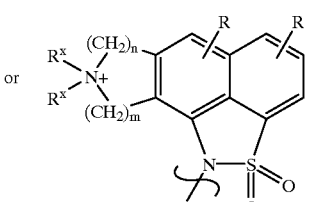

n = 0 to 4; m = 0 to 4
such that n + m = 2 to 4 n = 0 to 4; m = 0 to 4
such that n + m = 2 to 4 wherein:
each R is independently selected from: —$R^*$; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; — $C_{1-6}$ straight- or branched-chain alkyl, unsubstituted or substituted with one to four $R^d$ groups; and —$C_{3-7}$ cycloalkyl, unsubstituted or substituted with one to four $R^d$ groups;
each $R^a$, $R^b$ and $R^c$ independently represents hydrogen, —$R^*$, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;
or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;
or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;
each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —C($NR^e$)$NR^fR^g$; —$NR^eC(NH)NR^fR^g$; —$NR^eC(NR^f)R^g$; —$R^*$;
$R^e$, $R^f$ and $R^g$ represent hydrogen; —$R^*$; —$C_{1-6}$ straight- or branched-chain alkyl unsubstituted or substituted with one to four $R^i$ groups;
or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;
each $R^i$ independently represents halo; $C_{1-6}$ straight or branched chain alkyl; —CN; —$NO_2$; phenyl;

—NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

each R$^h$ independently represents hydrogen, —C$_{1-6}$ straight or branched-chain alkyl group, —C$_3$–C$_6$ cycloalkyl group or phenyl, or when two R$^h$ groups are present, said R$^h$ groups may be taken in combination and represent a 4–6 membered saturated ring, said saturated ring being optionally interrupted by one or two of O, S, SO$_2$, —C(O)—, NH and NCH$_3$;

R* is selected from the group consisting of:

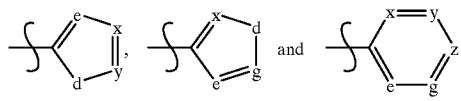

wherein:

d represents O, S or NR$^k$;

e, g, x, y and z represent CR$^m$, N or N$^+$R$^k$, provided that no more than one of e, g, x, y and z in any given structure represents N$^+$R$^k$;

R$^k$ represents hydrogen; —C$_{1-6}$ straight- or branched-chain alkyl, unsubstituted or substituted with one to four R$^i$ groups; or —(CH$_2$)$_n$Q where n=1, 2 or 3 and Q is as previously defined;

each R$^m$ independently represents a member selected from the group consisting of: hydrogen; halo; —CN; —NO$_2$; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^h$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$; —NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups;

R$^n$ and R$^o$ represent hydrogen, phenyl; —C$_{1-6}$ straight- or branched-chain alkyl unsubstituted or substituted with one to four R$^i$ groups;

each R$^w$ independently represents hydrogen; —C$_{1-6}$ straight- or branched-chain alkyl, C$_{3-6}$ cycloalkyl, said alkyl or cycloalkyl being optionally substituted with 1–4 R$^i$ groups; phenyl, or heteroaryl, said phenyl and heteroaryl being optionally substituted with 1–4 R$^i$ groups;

or R$^h$ and R$^w$ taken together with any intervening atoms represent a 5–6 membered saturated ring, optionally interrupted by one or two of O, S, SO$_2$, NH or NCH$_3$;

each R$^x$ independently represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said alkyl being unsubstituted or substituted with one to four of halo, CN, NO$_2$, OR$^w$, SR$^w$, SOR$^w$, SO$_2$R$^w$, NR$^h$R$^w$, N$^+$R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl or heteroaryl, said phenyl or heteroaryl is in turn optionally substituted with from one to four R$^i$ groups or with one to two C$_{1-3}$ straight- or branched-chain alkyl groups, said alkyl groups being unsubstituted or substituted with one to four R$^i$ groups;

or two R$^x$ groups taken together with any intervening atoms represent a 4–6 membered saturated ring optionally interrupted by O, S, SO$_2$, NR$^w$, N$^+$R$^w$R$^w$ or —C(O)—, said saturated ring being unsubstituted or substituted with 1–4 R$^i$ groups, where R$^w$ and R$^i$ are defined above, or two R$^w$ groups taken together with any intervening atoms represent a 4–6 membered saturated ring optionally interrupted by O, S, SO$_2$, NR$^h$, N$^+$R$^h$R$^h$ or —C(O)—, said saturated ring being unsubstituted or substituted with 1–4 R$^i$ groups, where R$^h$ and R$^i$ are defined above.

Pharmaceutical compositions and methods of treatment are also included herein.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups selected from R$^d$ and R$^i$ as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

  

pyrrole (pyrrolyl)   imidazole (imidazolyl)   thiazole (thiazolyl)

  

oxazole (oxazolyl)   furan (furyl)   thiophene (thienyl)

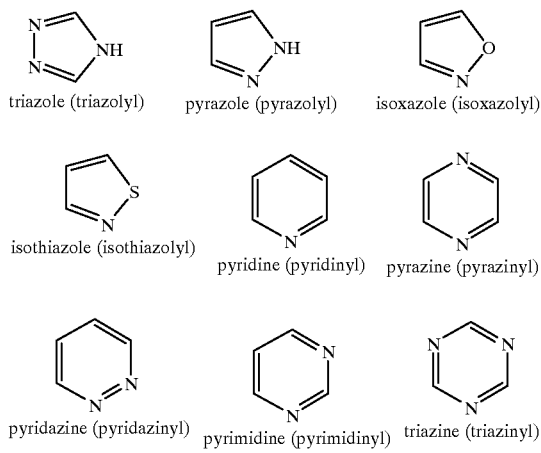

triazole (triazolyl)    pyrazole (pyrazolyl)    isoxazole (isoxazolyl)

isothiazole (isothiazolyl)    pyridine (pyridinyl)    pyrazine (pyrazinyl)

pyridazine (pyridazinyl)    pyrimidine (pyrimidinyl)    triazine (triazinyl)

Heteroarylium refers to heteroaryl groups bearing a quaternary nitrogen atom and thus a positive charge. Examples include the following:

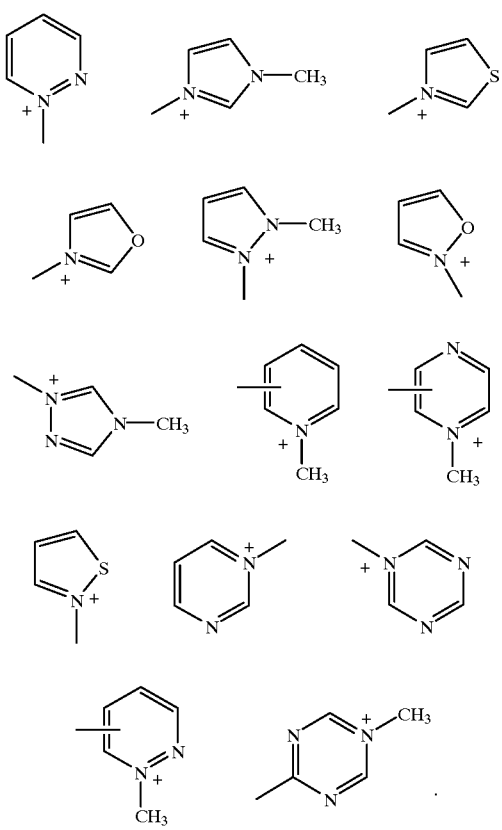

When a charge is shown on a particular nitrogen atom in a ring which contains one or more additional nitrogen atoms, it is understood that the charge may reside on a different nitrogen atom in the ring by virtue of charge resonance that occurs.

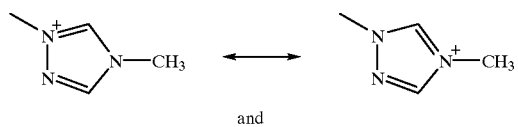

and

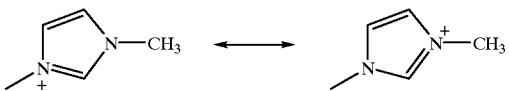

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methylpyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable C-6 hydroxyethyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$L^-$ can be present or absent as necessary to maintain the appropriate charge balance. When present, $L^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L– represents a specie with more than one negative charge, such as malonate, tartrate or ethylenediaminetetraacetate (EDTA), an appropriate number of carbapenem molecules can be found in association therewith to maintain the overall charge balance and neutrality.

A subset of compounds of formula I which is of interest relates to those compounds where $CO_2M$ represents a carboxylate anion. Hence, M in this instance represents a negative charge which will be balanced by a positively charged group, such as in the positively charged R side chain. Likewise, if the positively charged R side chain contains more than one positive charge, a negatively charged counterion may be present which in combination with the carboxylate anion, provides overall charge neutrality.

Another subset of compounds of formula I which is of interest relates to compounds of formula I wherein $R^x$ represents hydrogen or a $C_{1-8}$ straight- or branched-chain alkyl or two $R^x$ groups taken together with any intervening atoms represent a 4–6 membered saturated ring optionally interrupted by O, S, $SO_2$, $NR^w$, $N^+R^wR^w$ or —C(O)—, said alkyl or saturated ring being unsubstituted or substituted with 1–4 $R^i$ groups, where all other variables are defined above.

With respect to the positively charged moiety or moieties that are contained in one or more R or $R^x$ side chains, it is preferred that from 1–3 positive charges be present, and most preferably two or three positive charges be present, balanced by the carboxylate anion and a negatively charged counterion.

Another subset of compounds which is of interest is represented by formula I wherein one R group represents a H, —$C_{1-6}$ straight or branched chain alkyl group, substituted with one to four $R^d$ groups, wherein one $R^d$ group represents —R*.

Another group of compounds of interest is represented by formula I wherein one R* group is present and is selected from:

 and

Within this subset, d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

A preferred subset of compounds of the invention is represented by formula Ia:

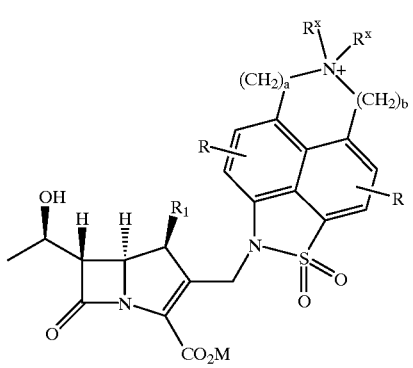

or a pharmaceutically acceptable salt thereof, wherein:
a=0 to 3 and b=0 to 3 such that a+b=1 to 3,
and all other variables are as originally defined.

A more preferred subset of formula Ia is realized when:
a=1 to 2 and b=1 to 2 such that a+b=2 to 3;
$CO_2M$ represents a carboxylate anion,
$R^1$ represents methyl;
and all other variables within this subset are as originally defined.

A still more preferred subset of formula Ia is realized when:
a=1 to 2 and b=1 to 2 such that a+b=2 to 3;
$CO_2M$ represents a carboxylate anion;
$R^1$ represents methyl;
each R represents hydrogen;
$R^h$ represents hydrogen or $C_{1-6}$ straight or branched chain alkyl group;
and all other variables within this subset are as originally defined.

Another preferred subset of the compounds of the compounds of the invention is represented by formula Ib:

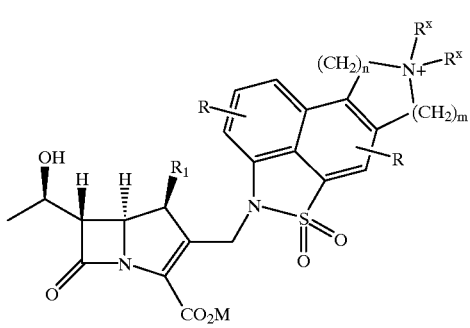

or a pharmaceutically acceptable salt thereof, wherein:
n=0 to 4 and m=0 to 4 such that n+m=2 to 4;
and all other variables are as originally defined.

A more preferred subset of compounds of formula Ib are realized when:

n=1 to 2 and m=1 to 2 such that n+m=2 to 4;
$CO_2M$ represents a carboxylate anion;
$R^1$ represents methyl;

and all other variables are as originally defined.

A still more preferred subset of formula Ib is realized when:

n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;

and all other variables within this subset are as originally defined.

Another preferred subset of compounds of the invention is represented by formula Ic:

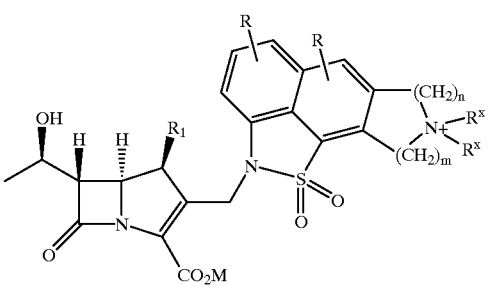

or a pharmaceutically acceptable salt thereof, wherein:

n=0 to 4 and m=0 to 4 such that n+m=2 to 4;

and all other variables are as described above.

Another more preferred subset of the compounds of formula Ic is realized when:

n=1 to 2 and m=1 to 2 such that n+m=2 to 4;
$CO_2M$ represents a carboxylate anion;
$R^1$ represents methyl;

and all other variables are as described above.

A still more preferred subset of the compounds of formula Ic is realized when:

n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;

and all other variables within this subset are as originally defined.

Another preferred subset of the compounds of the invention is represented by formula Id:

Id

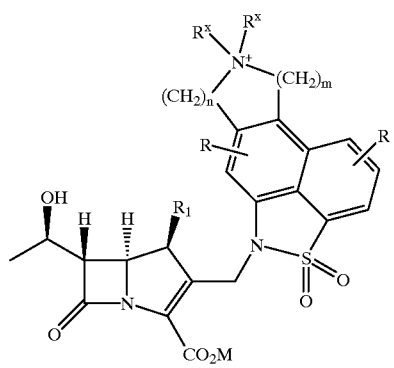

or a pharmaceutically acceptable salt thereof, wherein:
n=0 to 4 and m=0 to 4 such that n+m=2 to 4;
and all other variables are as described above.
A more preferred subset of the compounds of formula Id is realized when:
n=1 to 2 and m=1 to 2 such that n+m=2 to 4;
$CO_2M$ represents a carboxylate anion;
$R^1$ represents methyl;
and all other variables are as described above.
A still more preferred subset of formula Id is realized when:
n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;
and all other variables within this subset are as originally defined.

Another preferred subset of the compounds of the invention is represented by formula Ie:

Ie

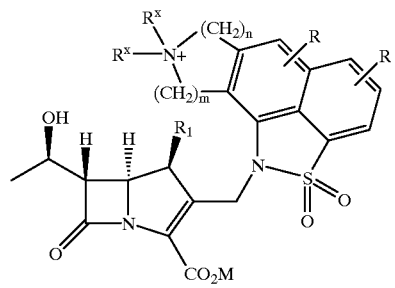

or a pharmaceutically acceptable salt thereof, wherein:
n=0 to 4 and m=0 to 4 such that n+m=2 to 4;
and all other variables are as described above.
A more preferred subset of the compounds formula Ie is realized when:
n=1 to 2 and m=1 to 2 such that n+m=2 to 4;
$CO_2M$ represents a carboxylate anion;
$R^1$ represents methyl;
and all other variables are as described above.
A still more preferred subset of the compounds of formula Ie is realized when:
n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;
and all other variables within this subset are as originally defined.

Representative examples of compounds of the present invention are as follows:

E-1

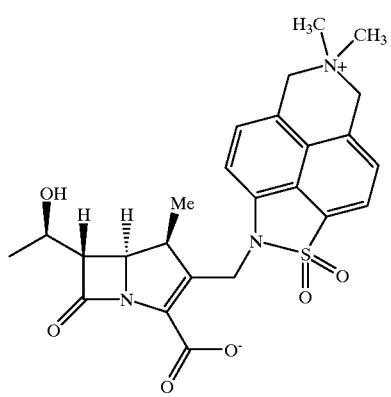

E-2

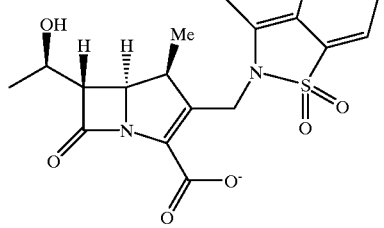

E-3

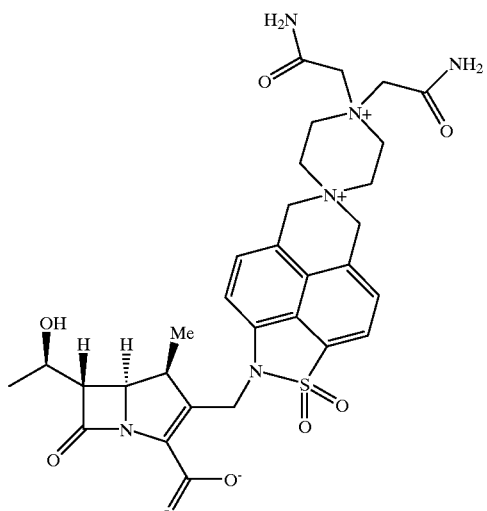

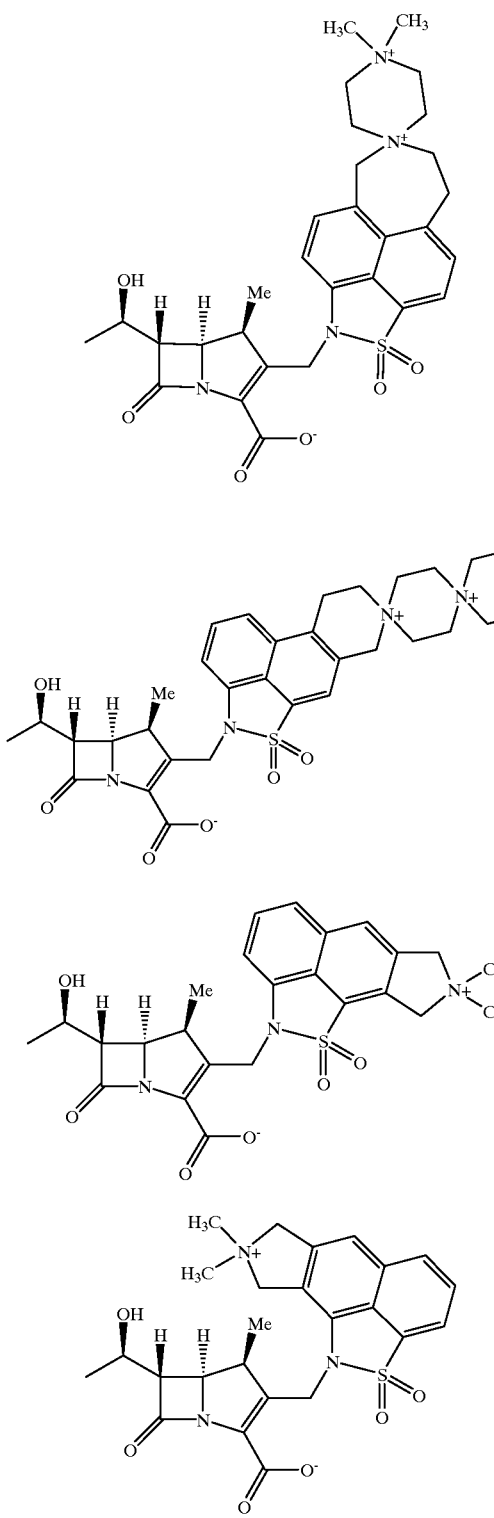

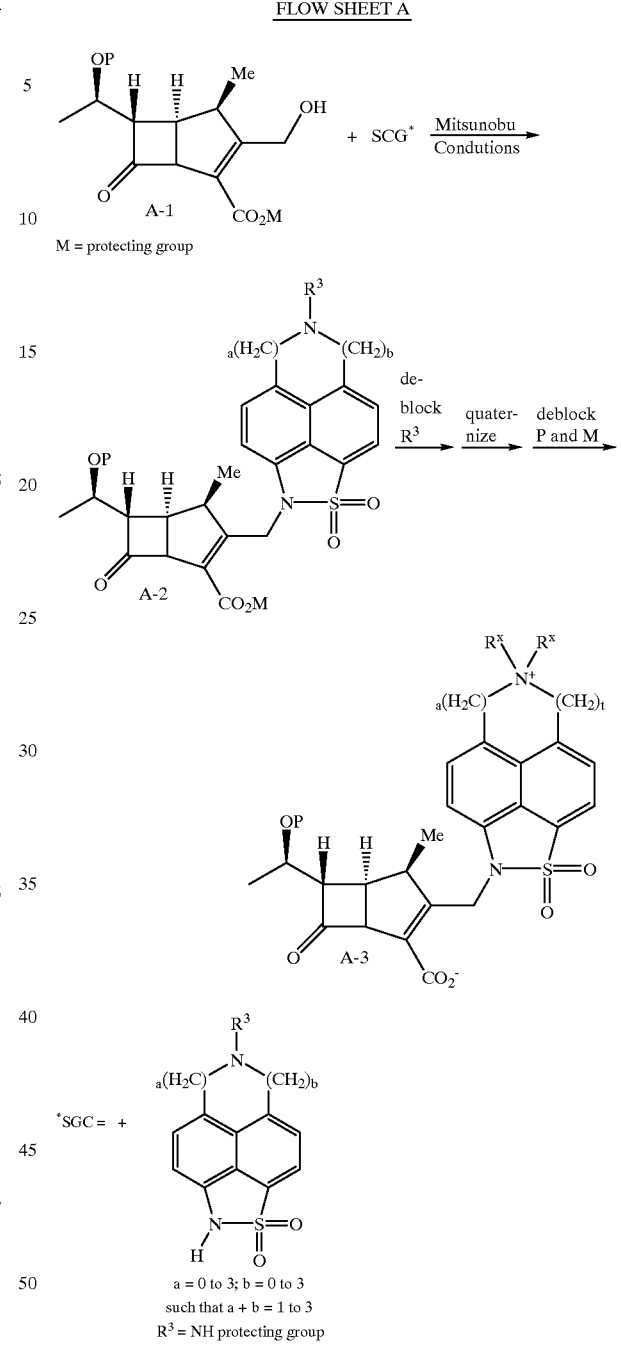

a = 0 to 3; b = 0 to 3
such that a + b = 1 to 3
$R^3$ = NH protecting group

The compounds of the present invention are prepared by reacting a suitably protected, activated 2-hydromethyl-carbapen-2-em-carboxylate with a napthosultam, modifying the thus-introduced sidechain as desired, and then removing any protecting groups which are present to afford the desired final product. The process is illustrated by the following generic scheme:

The naphthosultam side chain group (SCG) used in the synthesis of the compounds of the present invention have, in some cases, been described in the chemical literature. In other cases, precursor compounds which may be readily converted to the requisite naphthosultam have been described in the literature. In cases where the requisite naphthosultam is not known in the literature it is necessary to synthesize the naphthosultam by a newly developed synthesis. One skilled in the art can adapt a previously published synthesis of an analogous naphthosultam to prepare the requisite compound in a straightforward manner without undue experimentation. Numerous examples of naphthosultam synthesis are described herein (see below).

The naphthosultam side chain group (SCG) is initially reacted with a suitably protected carbapen-2-em-3-carboxylate having an activated hydroxymethyl group at the 2-position.

The carbapenem nucleus having a —CH$_2$OH substituent at position 2 can be obtained in accordance with Schmitt, S. M. et al., *J. Antibiotics* 41(6): 780–787 (1988), the teachings of which are incorporated herein by reference. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The addition of the naphthosultam side chain group (SCG) to the carbapenem is accomplished by treating a solution of the hydroxymethyl-carbapenem and the naphthosultam side chain group in a suitable solvent such as tetrahydrofuran (THF), ether, acetonitrile, dimethylformamide (DMF), benzene, dimethylsulfoxide (DMSO), and the like with a (premixed) suitable activating reagent such as diethyl azodicarboxylate (DEAD)/triphenylphosphine, diisopropyl azodicarboxylate (DIAD)/tributylphosphine, and the like, at a temperature between about −20° C. and 35° C. for about 5 to 90 minutes.

Alternatively, the naphthosultam and carbapenem can be mixed together with either the azodicarboxylate or the phosphine reagent in a suitable and the other component of the activating reagent (the phosphine or the azodicarboxylate, respectively) can be added to that mixture. Once the naphthosultam, carbapenem, and activating reagent(s) have been mixed, the reaction is allowed to proceed at a temperature between about −20° C. and 35° C. for about 5 to 90 minutes.

The resulting mixture is then subjected to a standard work-up procedure familiar to those skilled in the art to afford a crude 2-naphthosultam-methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

The synthesis of the target compound is completed by removing any protecting groups which are present in the penultimate intermediate using standard techniques which are well known to those skilled in the art. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples and preparative examples, which disclose the syntheses of claimed compounds and requisite starting materials.

PREPARATIVE EXAMPLE 1

Synthesis of 2,5,6,7-tetrahydro-1-thia-2,6-diaza-cyclopenta[cd]phenalene 1,1 Dioxide

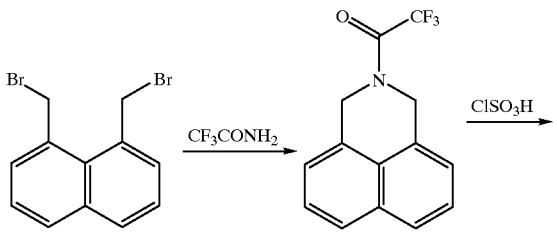

-continued

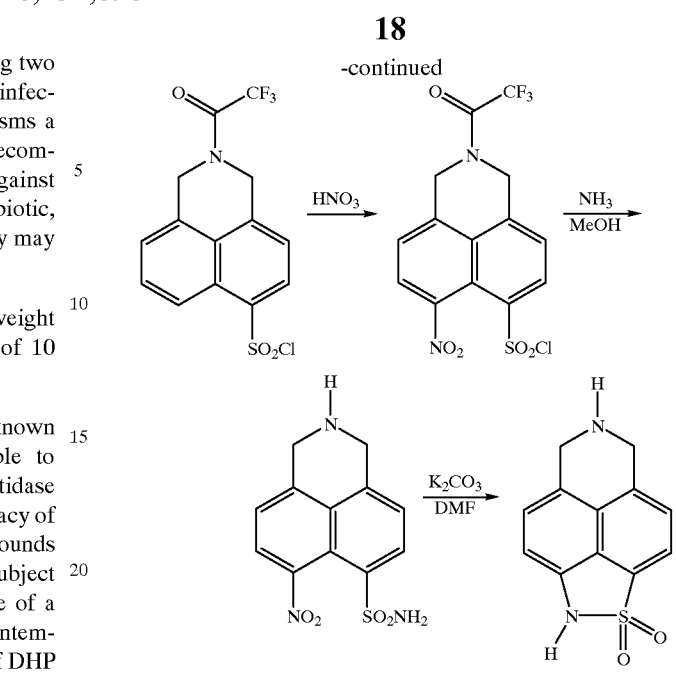

Step 1: Preparation of 2,3-dihydro-2-trifluoroacetyl-1H-Benz[de]isoquinoline

Trifluoroacetamide (10 mmol) is reacted with 1,8-bis (bromomethyl)naphthalene (10 mmol) and sodium hydride (10 mmol) in DMF according to the procedure of Wright et al (Biochim. Biophys. Acta 1990, 1040, 95–101) to afford the title compound.

Step 2: Preparation of 2,3-dihydro-2-trifluoroacetyl-1H-Benz[de]isoquinoline-6-sulfonyl Chloride Chlorosulfonic acid (40 mmol) is added dropwise to a cold (0° C.) solution of 2,3-dihydro-2-trifluoroacetyl-1H-Benz[de]isoquinoline (8 mmol) in chloroform (800 mL). The resulting solution is stirred at 0° C. for 30 minutes. The cold bath is then removed and the solution is stirred at room temperature for 1 hour then cautiously poured into ice-water. The organic layer is separated, dried over magnesium sulfate and concentrated to afford the title compound. The crude product can be purified by recrystallization or chromatography.

Step 3: Preparation of 7-nitro-2,3-dihydro-2-trifluoroacetyl-1H-Benz[de]isoquinoline-6-sulfonyl Chloride Solid 2,3-dihydro-2-trifluoroacetyl-1H-Benz[de] isoquinoline-6-sulfonyl chloride (6 mmol) is added portionwise to cold (0° C.) 90% nitric acid (5 mL). The resulting mixture is stirred at 0° C. overnight then cautiously poured into ice-water. The precipitate is collected by filtration and washed with ice-water to give the title compound. The crude product can be purified by recrystallization or chromatography.

Step 4: Preparation of 7-nitro-2,3-dihydro-1H-Benz[de] isoquinoline-6-sulfonic Acid Amide A 2M solution of ammonia in methanol (10 mL) is added to a solution of 7-nitro-2,3-dihydro-2-trifluoroacetyl-1H-Benz[de]isoquinoline-6-sulfonyl chloride (4 mmol) in 40 mL of methanol and the resulting mixture is stirred at room temperature for 24 hours. The mixture is then concentrated under vacuum and the residue is partitioned between ethyl acetate and water. The organic layer is dried over magnesium sulfate and concentrated to afford the title compound. The crude product can be purified by recrystallization or chromatography.

Step 5: Preparation of 2,5,6,7-tetrahydro-1-thia-2,6-diaza-cyclopenta[cd]phenalene 1,1-dioxide Potassium carbonate (15 mmol) is added to a solution of 7-nitro-2,3-dihydro-1H-Benz[de]isoquinoline-6-sulfonic acid amide (3 mmol) in anhydrous DMF (30 mL). The resulting solution is stirred at 100° C. for 12 hours then partitioned between ethyl acetate and water. The organic layer is dried over magnesium sulfate and concentrated to afford the title compound. The crude product can be purified by recrystallization or chromatography.

PREPARATIVE EXAMPLE 2

Synthesis of 8,9-dihydro-4H,7H-5-thia-4,8-diaza-cyclopenta[e]-acenaphthy-lene 5,5-dioxide

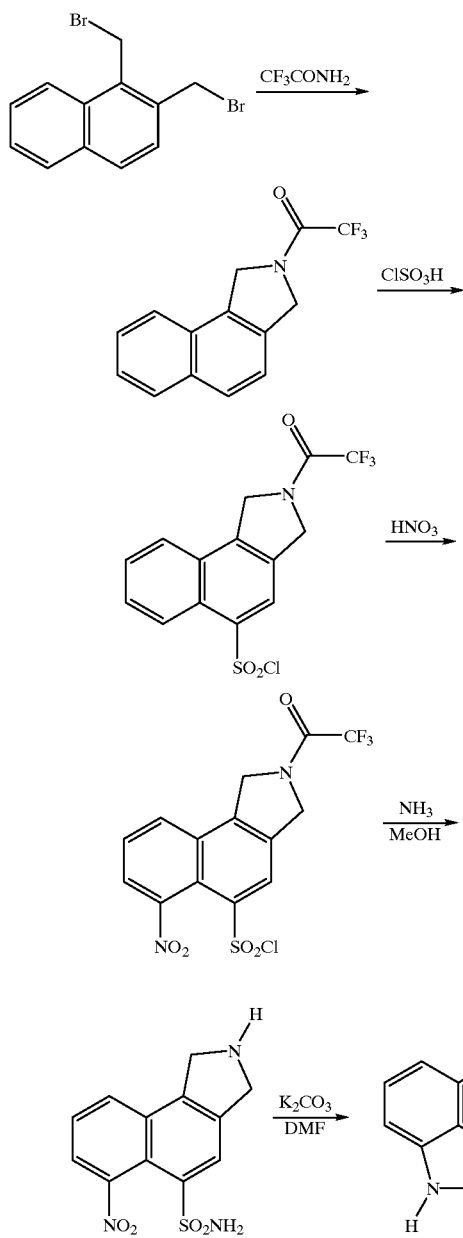

Step 1: Preparation of 1-(1,3-dihydro-benzo[e]isoindol-2-yl)-2,2,2-trifluoro-ethanone Substitution of 1,2-bis(bromomethyl)naphthalene for 1,8-bis(bromomethyl)naphthalene in the procedure of Step 1 of Preparative Example 1 affords the title compound. The crude product can be purified by recrystallization or chromatography.

Step 2: Preparation of 2-trifluoroacetyl-2,3-dihydro-1H-benzo[e]isoindole-5-sulfonyl Chloride Substitution of 1-(1,3-dihydro-benzo[e]isoindol-2-yl)-2,2,2-trifluoro-ethanone for 2,3-dihydro-2-trifluoroacetyl-1H-Benz[de]isoquinoline in the procedure of Step 2 of Preparative Example 1 affords the title compound. The crude product can be purified by recrystallization or chromatography.

Step 3: Preparation of 6-nitro-2-trifluoroacetyl-2,3-dihydro-1H-benzo[e]isoindole-5-sulfonyl Chloride Substitution of 2-trifluoroacetyl-2,3-dihydro-1H-benzo[e]isoindole-5-sulfonyl chloride for 2,3-dihydro-2-trifluoroacetyl-1H-Benz[de]isoquinoline-6-sulfonyl chloride in the procedure of Step 3 of Preparative Example 1 affords the title compound. The crude product can be purified by recrystallization or chromatography.

Step 4: Preparation of 6-nitro-2,3-dihydro-1H-benzo[e]isoindole-5-sulfonic Acid Amide Substitution of 6-nitro-2-trifluoroacetyl-2,3-dihydro-1H-benzo[e]isoindole-5-sulfonyl chloride for 7-nitro-2,3-dihydro-2-trifluoroacetyl-1H-Benz[de]isoquinoline-6-sulfonyl chloride in the procedure of Step 4 of Preparative Example 1 affords the title compound. The crude product can be purified by recrystallization or chromatography.

Step 5: Preparation of 8,9-dihydro-4H,7H-5-thia-4,8-diaza-cyclopenta[e]acenaphthylene 5,5-dioxide Substitution of 6-nitro-2,3-dihydro-1H-benzo[e]isoindole-5-sulfonic acid amide for 7-nitro-2,3-dihydro-1H-Benz[de]isoquinoline-6-sulfonic acid amide in the procedure of Step 5 of Preparative Example 1 affords the title compound. The crude product can be purified by recrystallization or chromatography.

PREPARATIVE EXAMPLE 3

Synthesis of 7,8,9,10-tetrahydro-4H-5-thia-4,8-diaza-acephenanthrylene 5,5-dioxide

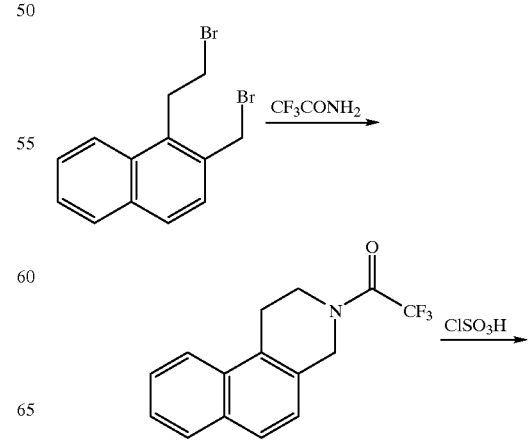

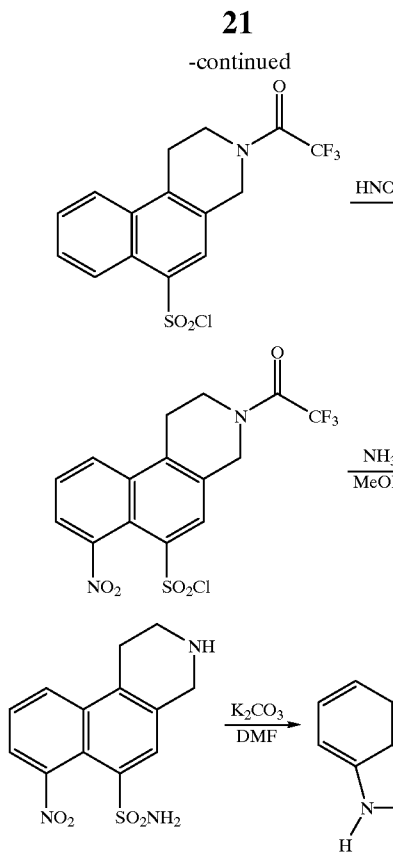

1H-Benz[de]isoquinoline-6-sulfonic acid amide in the procedure of Step 5 of Preparative Example 1 affords the title compound. The crude product can be purified by recrystallization or chromatography.

PREPARATIVE EXAMPLE 4

Synthesis of 2,7,8,9-tetrahydro-1-thia-2,8-diaza-cyclopenta[d]acenaphthylene 1,1-dioxide

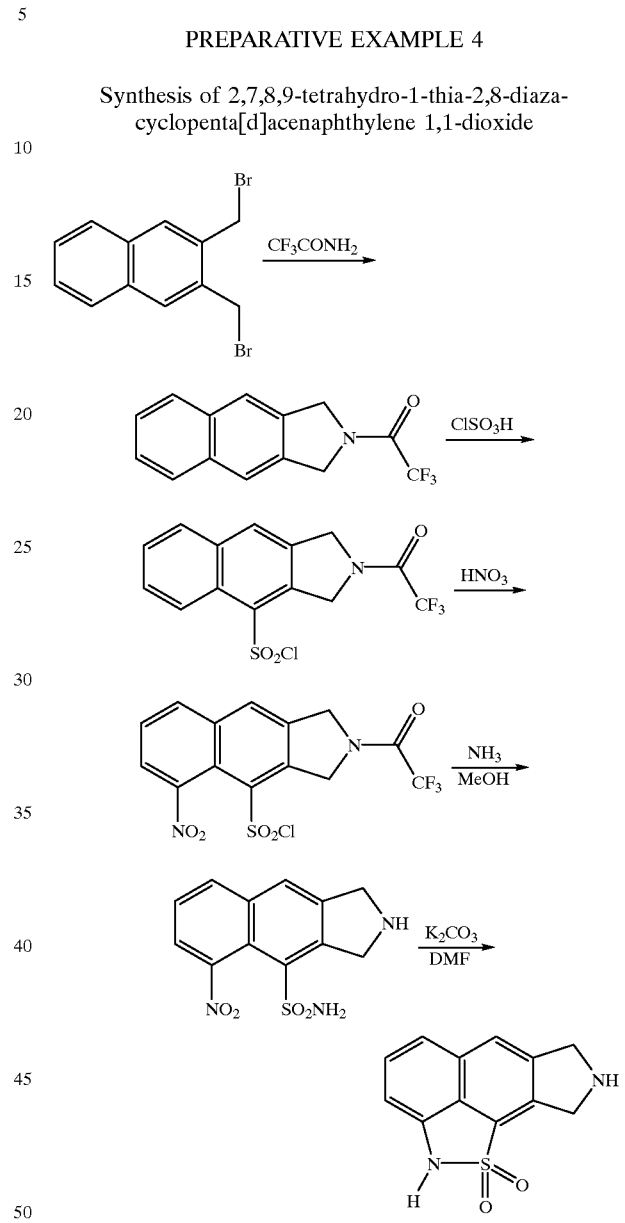

Step 1: Preparation of 1-(1,4-dihydro-2H-benzo[f]isoquinolin-3-yl)-2,2,2-trifluoro-ethanone Substitution of 1-(2-bromo-ethyl)-2-bromomethyl-naphthalene for 1,8-bis(bromomethyl)naphthalene in the procedure of Step 1 of Preparative Example 1 affords the title compound. The crude product can be purified by recrystallization or chromatography.

Step 2: Preparation of 3-trifluoroacetyl-1,2,3,4-tetrahydro-benzo[f]isoquinoline-6-sulfonyl Chloride Substitution of 1-(1,4-dihydro-2H-benzo[f]isoquinolin-3-yl)-2,2,2-trifluoro-ethanone for 2,3-dihydro-2-trifluoroacetyl-1H-Benz[de]isoquinoline in the procedure of Step 2 of Preparative Example 1 affords the title compound. The crude product can be purified by recrystallization or chromatography.

Step 3: Preparation of 7-nitro-3-trifluoroacetyl-1,2,3,4-tetrahydro-benzo[f]isoquinoline-6-sulfonyl Chloride Substitution of 3-trifluoroacetyl-1,2,3,4-tetrahydro-benzo[f]isoquinoline-6-sulfonyl chloride for 2,3-dihydro-2-trifluoroacetyl-1H-Benz[de]isoquinoline-6-sulfonyl chloride in the procedure of Step 3 of Preparative Example 1 affords the title compound. The crude product can be purified by recrystallization or chromatography.

Step 4: Preparation of 7-nitro-1,2,3,4-tetrahydro-benzo[f]isoquinoline-6-sulfonic Acid Amide Substitution of 7-nitro-3-trifluoroacetyl-1,2,3,4-tetrahydro-benzo[f]isoquinoline-6-sulfonyl chloride for 7-nitro-2,3-dihydro-2-trifluoroacetyl-1H-Benz[de]isoquinoline-6-sulfonyl chloride in the procedure of Step 4 of Preparative Example 1 affords the title compound. The crude product can be purified by recrystallization or chromatography.

Step 5: Preparation of 7,8,9,10-tetrahydro-4H-5-thia-4,8-diaza-acephenanthrylene 5,5-dioxide Substitution of 7-nitro-1,2,3,4-tetrahydro-benzo[f]isoquinoline-6-sulfonic acid amide for 7-nitro-2,3-dihydro-1H-Benz[de]isoquinoline-6-sulfonic acid amide in the procedure of Step 5 of Preparative Example 1 affords the title compound. The crude product can be purified by recrystallization or chromatography.

Step 1: Preparation of 1-(1,3-dihydro-benzo[f]isoindol-2-yl)-2,2,2-trifluoro-ethanone Substitution of 2,3-bis(bromomethyl)naphthalene for 1,8-bis(bromomethyl)naphthalene in the procedure of Step 1 of Preparative Example 1 affords the title compound. The crude product can be purified by recrystallization or chromatography.

Step 2: Preparation of 2-trifluoroacetyl-2,3-dihydro-1H-benzo[f]isoindole-4-sulfonyl Chloride Substitution of 1-(1,3-dihydro-benzo[f]isoindol-2-yl)-2,2,2-trifluoro-ethanone for 2,3-dihydro-2-trifluoroacetyl-1H-Benz[de]isoquinoline in the procedure of Step 2 of Preparative Example 1 affords the title compound. The crude product can be purified by recrystallization or chromatography.

Step 3: Preparation of 5-nitro-2-trifluoroacetyl-2,3-dihydro-1H-benzo[f]isoindole-4-sulfonyl Chloride Substitution of 2-trifluoroacetyl-2,3-dihydro-1H-benzo[f]isoindole-4-sulfonyl chloride for 2,3-dihydro-2-trifluoroacetyl-1H-Benz[de]isoquinoline-6-sulfonyl chloride in the procedure of Step 3 of Preparative Example 1 affords the title compound. The crude product can be purified by recrystallization or chromatography.

Step 4: Preparation of 5-nitro-2,3-dihydro-1H-benzo[f]isoindole-4-sulfonic Acid Amide Substitution of 5-nitro-2-trifluoroacetyl-2,3-dihydro-1H-benzo[f]isoindole-4-sulfonyl chloride for 7-nitro-2,3-dihydro-2-trifluoroacetyl-1H-Benz[de]isoquinoline-6-sulfonyl chloride in the procedure of Step 4 of Preparative Example 1 affords the title compound. The crude product can be purified by recrystallization or chromatography.

Step 5: Preparation of 2,7,8,9-tetrahydro-1-thia-2,8-diaza-cyclopenta[d]acenaphthylene 1,1-dioxide Substitution of 5-nitro-2,3-dihydro-1H-benzo[f]isoindole-4-sulfonic acid amide for 7-nitro-2,3-dihydro-1H-Benz[de]isoquinoline-6-sulfonic acid amide in the procedure of Step 5 of Preparative Example 1 affords the title compound. The crude product can be purified by recrystallization or chromatography.

PREPARATIVE EXAMPLE 5

Synthesis of 8,9-dihydro-5H,7H-4-thia-5,8-diaza-cyclopenta[e]acenaphthylene 4,4-dioxide

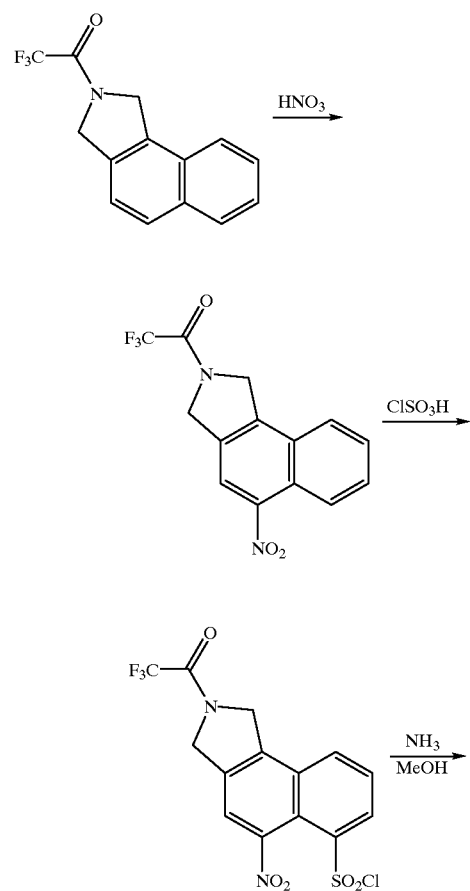

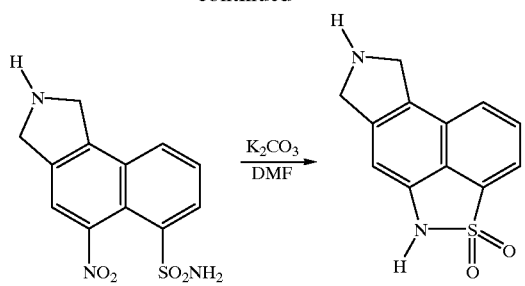

Step 1: Preparation of 5-nitro-2-trifluoroacetyl-2,3-dihydro-1H-benzo[e]isoindole Substitution of 1-(1,3-dihydro-benzo[e]isoindol-2-yl)-2,2,2-trifluoro-ethanone for 2,3-dihydro-2-trifluoroacetyl-1H-Benz[de]isoquinoline-6-sulfonyl chloride in the procedure of Step 3 of Preparative Example 1 affords the title compound. The crude product can be purified by recrystallization or chromatography.

Step 2: Preparation of 5-nitro-2-trifluoroacetyl-2,3-dihydro-1H-benzo[e]isoindole-6-sulfonyl Chloride Substitution of 5-nitro-2-trifluoroacetyl-2,3-dihydro-1H-benzo[e]isoindole for 2,3-dihydro-2-trifluoroacetyl-1H-Benz[de]isoquinoline in the procedure of Step 2 of Preparative Example 1 affords the title compound. The crude product can be purified by recrystallization or chromatography.

Step 3: Preparation of 5-nitro-2,3-dihydro-1H-benzo[e]isoindole-6-sulfonic Acid Amide Substitution of 5-nitro-2-trifluoroacetyl-2,3-dihydro-1H-benzo[e]isoindole-6-sulfonyl chloride for 7-nitro-2,3-dihydro-2-trifluoroacetyl-1H-Benz[de]isoquinoline-6-sulfonyl chloride in the procedure of Step 4 of Preparative Example 1 affords the title compound. The crude product can be purified by recrystallization or chromatography.

Step 4: Preparation of 8,9-dihydro-5H,7H-4-thia-5,8-diaza-cyclopenta[e]acenaphthylene 4,4-dioxide Substitution of 5-nitro-2,3-dihydro-1H-benzo[e]isoindole-6-sulfonic acid amide for 7-nitro-2,3-dihydro-1H-Benz[de]isoquinoline-6-sulfonic acid amide in the procedure of Step 5 of Preparative Example 1 affords the title compound. The crude product can be purified by recrystallization or chromatography.

PREPARATIVE EXAMPLE 6

Synthesis of 8,9-dihydro-1H,7H-2-thia-1,8-diaza-cyclopenta[d]acenaphthylene 2,2-dioxide

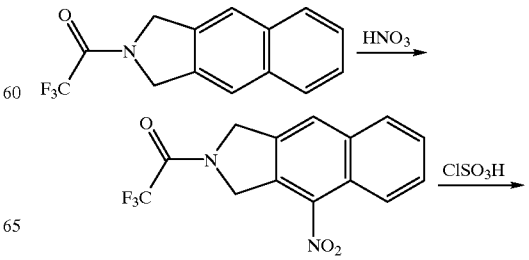

25
-continued

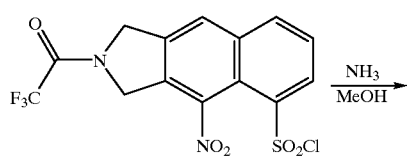

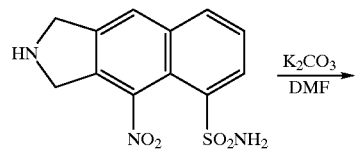

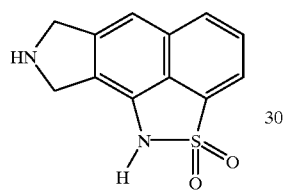

Step 1: Preparation of 4-nitro-2-trifluoroacetyl-2,3-dihydro-1H-benzo[f]isoindole Substitution of 1-(1,3-dihydro-benzo[f]isoindol-2-yl)-2,2,2-trifluoro-ethanone for 2,3-dihydro-2-trifluoroacetyl-1H-Benz[de]isoquinoline-6-sulfonyl chloride in the procedure of Step 3 of Preparative Example 1 affords the title compound. The crude product can be purified by recrystallization or chromatography.

Step 2: Preparation of 4-nitro-2-trifluoroacetyl-2,3-dihydro-1H-benzo[f]isoindole-5-sulfonyl Chloride Substitution of 4-nitro-2-trifluoroacetyl-2,3-dihydro-1H-benzo[f]isoindole for 2,3-dihydro-2-trifluoroacetyl-1H-Benz[de]isoquinoline in the procedure of Step 2 of Preparative Example 1 affords the title compound. The crude product can be purified by recrystallization or chromatography.

Step 3: Preparation of 4-nitro-2,3-dihydro-1H-benzo[f]isoindole-5-sulfonic Acid Amide Substitution of 4-nitro-2-trifluoroacetyl-2,3-dihydro-1H-benzo[f]isoindole-5-sulfonyl chloride for 7-nitro-2,3-dihydro-2-trifluoroacetyl-1H-Benz[de]isoquinoline-6-sulfonyl chloride in the procedure of Step 4 of Preparative Example 1 affords the title compound. The crude product can be purified by recrystallization or chromatography.

Step 4: Preparation of 8,9-dihydro-1H,7H-2-thia-1,8-diaza-cyclopenta[d]acenaphthylene 2,2-dioxide Substitution of 4-nitro-2,3-dihydro-1H-benzo[f]isoindole-5-sulfonic acid amide for 7-nitro-2,3-dihydro-1H-Benz[de]isoquinoline-6-sulfonic acid amide in the procedure of Step 5 of Preparative Example 1 affords the title compound. The crude product can be purified by recrystallization or chromatography.

26
EXAMPLE 1

Synthesis of (1S,5R,6S)-1-methyl-2-(1,1-dioxo-2,5,6,7-tetrahydro-1-thia-2-aza-6-azonia-6,6-dimethyl-cyclopenta[cd]phenalen-2-ylmethyl)-6-(1-(R)-hydroxyethyl)-carbapen-2-em-3-carboxylate

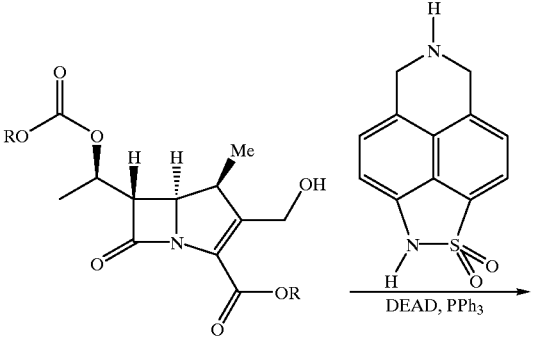

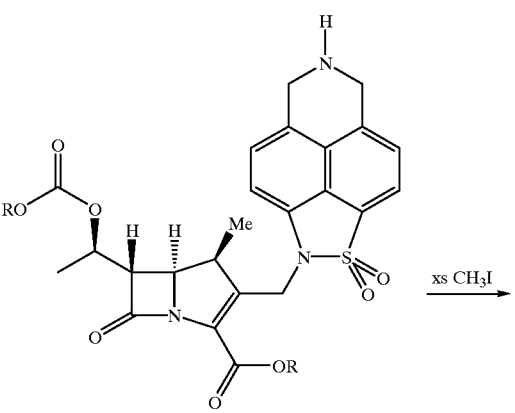

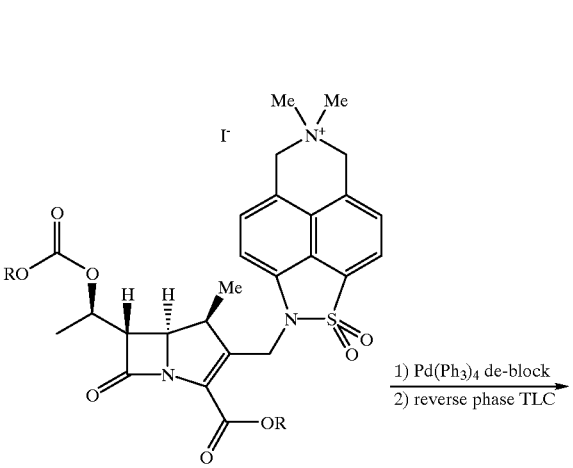

-continued

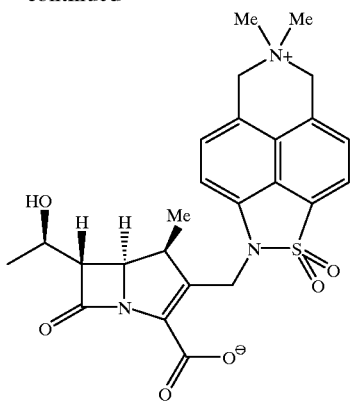

Step 1: Allyl (1S,5R,6S)-1-methyl-2-(1,1-dioxo-2,5,6,7-tetrahydro-1-thia-2,6-diaza-cyclopenta[cd]phenalen-2-ylmethyl)-6-(1-(R)-allyloxycarbonyloxyethyl)-carbapen-2-em-3-carboxylate Diethylazodicarboxylate (2.25 mmol) is added to a cold (0° C.) solution of allyl (1S,5R,6S)-2-(hydroxymethyl)-6-[1(R)-allyloxycarbonyloxy-ethyl]-1-methylcarbapen-2-em-3-carboxylate (1.5 mmol), 2,5,6,7-tetrahydro-1-thia-2,6-diaza-cyclopenta[cd]phenalene-1,1-dioxide (1.5 mmol) and triphenylphosphine (2.25 mmol) in tetrahydrofuran (15 mL). The mixture is stirred at room temperature for 30 minutes then partitioned between ethyl acetate (100 mL) and water (100 mL). The water layer is extracted with ethyl acetate (50 mL) and the combined ethyl acetate layers are washed with saturated aqueous sodium chloride (50 mL), dried with magnesium sulfate, filtered, and evaporated. The crude product is purified by column chromatography to give the title compound.

Step 2: Allyl (1S,5R,6S)-1-methyl-2-(1,1-dioxo-2,5,6,7-tetrahydro-1-thia-2-aza-6-azonia-6,6-dimethyl-cyclopenta[cd]phenalen-2-ylmethyl)-6-(1-(R)-allyloxycarbonyloxyethyl)-carbapen-2-em-3-carboxylate Methyl iodide (3 mmol) and sodium hydride (1 mmol) are added to a solution of allyl (1S,5R,6S)-1-methyl-2-(1,1-dioxo-2,5,6,7-tetrahydro-1-thia-2,6-diaza-cyclopenta[cd]phenalen-2-ylmethyl)-6-(1-(R)-allyloxycarbonyloxy-ethyl)-carbapen-2-em-3-carboxylate (1 mmol) in ether (10 mL). The reaction mixture is stirred at room temperature for 24 hours then the precipitate is collected by filtration. The crude product thus obtained is used in the next step without purification.

Step 3: (1S,5R,6S)-1-methyl-2-(1,1-dioxo-2,5,6,7-tetrahydro-1-thia-2-aza-6-azonia-6,6-dimethyl-cyclopenta[cd]phenalen-2-ylmethyl)-6-(1-(R-hydroxyethyl)-carbapen-2-em-3-carboxylate Ethyl hexanoic acid (0.55 mmol) and a 0.5M solution of sodium ethyl hexanoate in ethyl acetate (1.1 mL, 0.55 mmol) are added to a cold (0° C.) solution of allyl (1S,5R,6S)-1-methyl-2-(1,1-dioxo-2,5,6,7-tetrahydro-1-thia-2-aza-6-azonia-6,6-dimethyl-cyclopenta[cd]phenalen-2-ylmethyl)-6-(1-(R)-allyloxycarbonyloxy-ethyl)-carbapen-2-em-3-carboxylat (0.5 mmol) in dimethylformamide (5 mL). The mixture is put under a nitrogen atmosphere using a Firestone valve then triphenylphosphine (0.15 mmol) and tetrakis(triphenylphosphine)palladium (0.15 mmol) are added. The mixture is stirred at 0° C. for one hour then diethyl ether (50 mL) is added. The precipitate is collected by filtration, washed with cold diethyl ether (50 mL) and dried under vacuum. The solid is purified on 1000 micron reversed phase silica gel TLC plates developed with 30% acetonitrile/water. The band containing the title compound is eluted with 80% acetonitrile/water. The eluent is diluted with water the washed with hexane and concentrated to approximately 1 mL which is lyophilized to give the purified title compound.

EXAMPLES 2–6

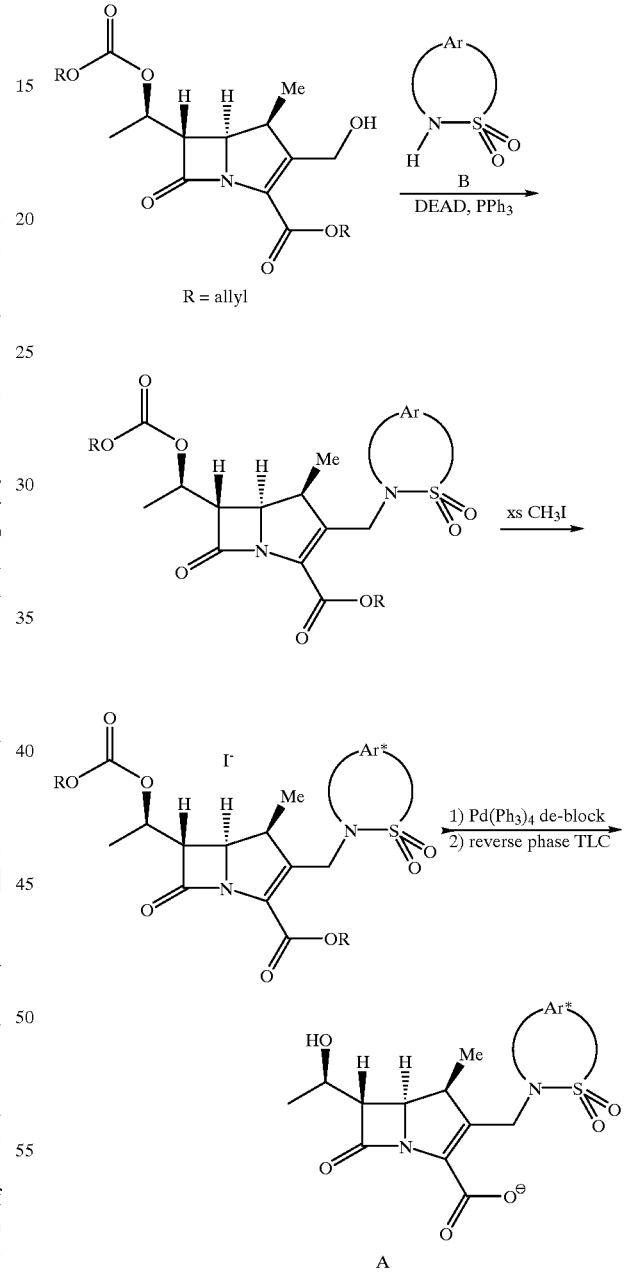

By appropriately modifying the procedure of Example 1, allyl (1S,5R,6S)-2-(hydroxymethyl)-6-[1(R)-allyloxycarbonyloxy-ethyl]-1-methylcarbapen-2-em-3-carboxylate is reacted with the side chain (compound B) as set forth in the following Table to produce compounds of formula A.

TABLE
| Example # | B | Ar* |
|---|---|---|
| 2 | 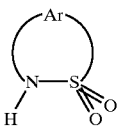 | 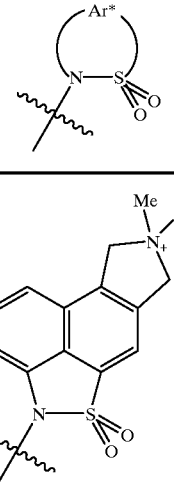 |
| 3 | 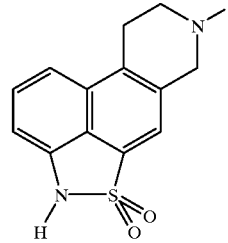 | 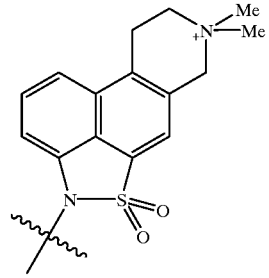 |
| 4 | 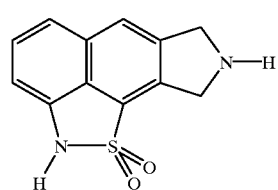 | 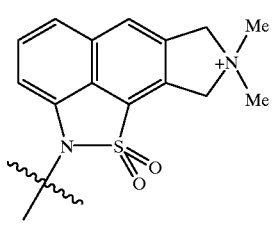 |
| 5 | 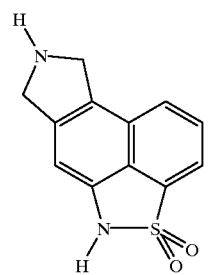 | 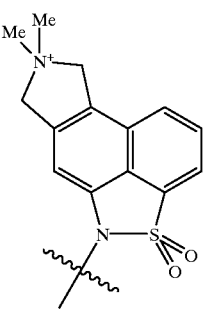 |
| 6 | 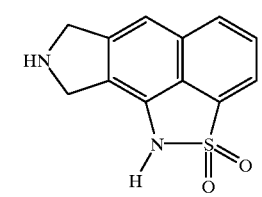 | 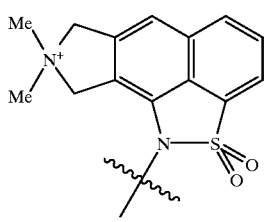 |

EXAMPLE 7

Synthesis of (1S,5R,6S)-1-methyl-2-(Spiro[3'-azonia-3',3'-dimethyl-1',6-1,1-dioxo-2,5,6,7-tetrahydro-1-thia-2-aza-6-azonia-6,6-dimethyl-cyclopenta[cd]phenalen-2-yl]methyl)-6-(1-(R)-hydroxyethyl)-carbapen-2-em-3-carboxylate Chloride

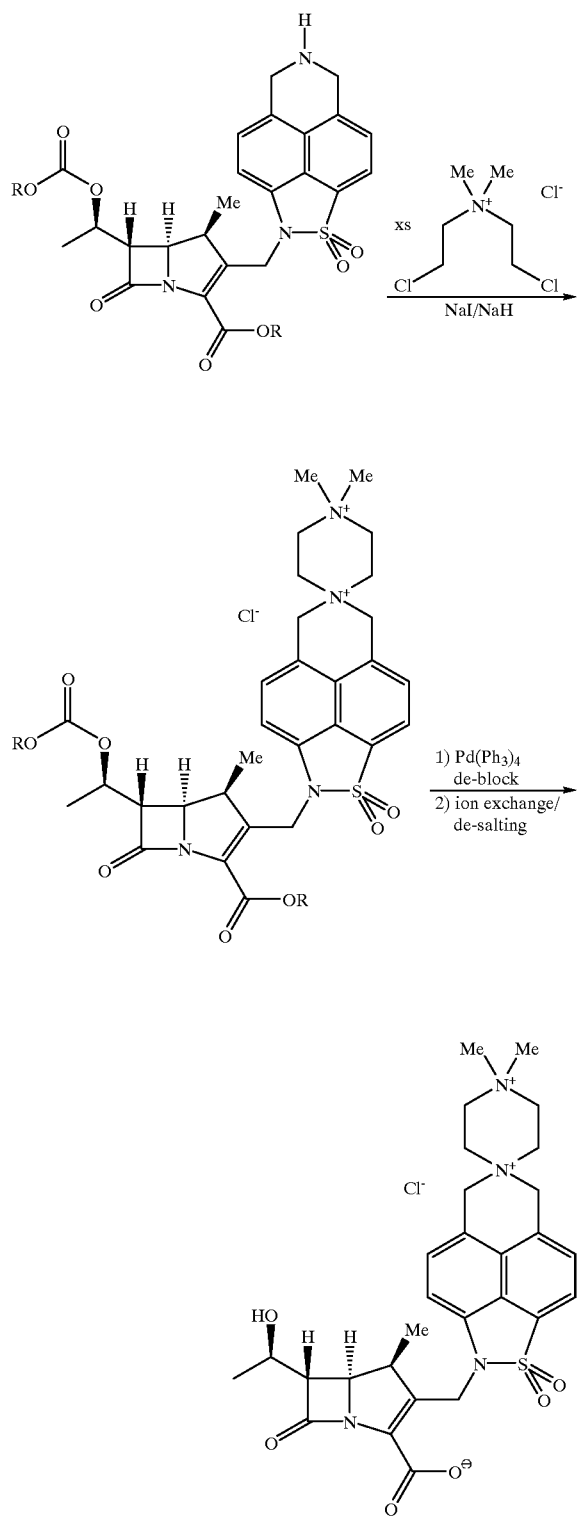

Step 1: Allyl (1S,5R,6S)-1-methyl-2-(Spiro[3'-azonia-3',3'-dimethyl-1',6-1,1-dioxo-2,5,6,7-tetrahydro-1-thia-2-aza-6-azonia-6,6-dimethyl-cyclopenta[cd]phenalen-2-yl]methyl)-6-(1-(R)-allyloxycarbonyloxy-ethyl)-carbapen-2-em-3-carboxylate Chloride Bis(2-chloroethyl)dimethyl ammonium chloride (3 mmol), sodium iodide (3 mmol), and sodium hydride (1 mmol) are added to a solution of allyl (1S,5R,6S)-1-methyl-2-(1,1-dioxo-2,5,6,7-tetrahydro-1-thia-2,6-diaza-cyclopenta[cd]phenalen-2-ylmethyl)-6-(1-(R)-allyloxycarbonyloxy-ethyl)-carbapen-2-em-3-carboxylate (1 mmol) in tetrahydrofuran (10 mL). The reaction mixture is stirred at room temperature for 24 hours then the precipitate is collected by filtration. The crude product thus obtained is used in the next step without purification.

Step 2: (1S,5R,6S)-1-methyl-2-(Spiro[3'-azonia-3',3'-dimethyl-1',6-1,1-dioxo-2,5,6,7-tetrahydro-1-thia-2-aza-6-azonia-6,6-dimethyl-cyclopenta[cd]phenalen-2-yl]methyl)-6-(1-(R)-hydroxyethyl)-carbapen-2-em-3-carboxylate Chloride Ethyl hexanoic acid (0.55 mmol) and a 0.5M solution of sodium ethyl hexanoate in ethyl acetate (1.1 mL, 0.55 mmol) are added to a cold (0° C.) solution of allyl (1S,5R,6S)-1-methyl-2-(Spiro[3'-azonia-3',3'-dimethyl-1',6-1,1-dioxo-2,5,6,7-tetrahydro-1-thia-2-aza-6-azonia-6,6-dimethyl-cyclopenta[cd]phenalen-2-yl]methyl)-6-(1-(R)-allyloxycarbonyloxy-ethyl)-carbapen-2-em-3-carboxylate chloride (0.5 mmol) in dimethylformamide (5 mL). The mixture is put under a nitrogen atmosphere using a Firestone valve then triphenylphosphine (0.15 mmol) and tetrakis(triphenylphosphine)palladium (0.15 mmol) are added. The mixture is stirred at 0° C. for one hour then diethyl ether (50 mL) is added. The precipitate is collected by filtration, washed with cold diethyl ether (50 mL) and dried under vacuum. The solid is dissolved in 1:1 acetonitrile/water and is loaded onto a Bio-Rad weak cation exchange resin (macroprep cm ion exchange resin, sodium cycle). The column is washed with 1:1 acetonitrile/water followed by water. The column is then eluted with 5% aqueous sodium chloride. The fractions containing the title compound are cooled in an ice bath and loaded onto an amberchrom CG-161 resin. The column is washed with cold de-ionized water and then eluted with 20% isopropanol in water. The fractions containing the title compound are combined and concentrated to approximately 1 mL which is lyophilized to give the purified title compound.

EXAMPLES 8–12

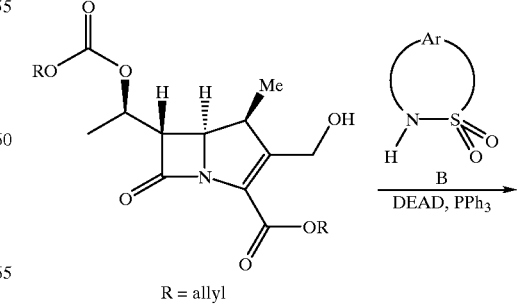

R = allyl

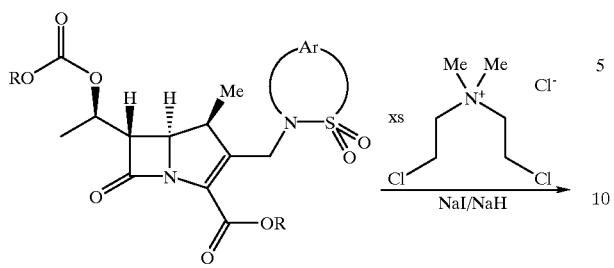
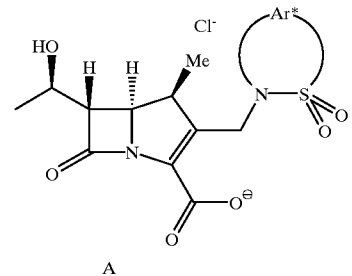
A
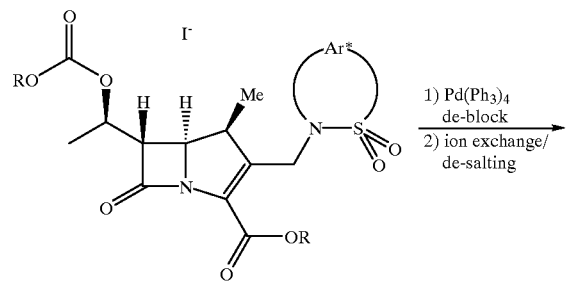
By appropriately modifying the procedure of Examples 1 and 7, allyl (1S,5R,6S)-2-(hydroxymethyl)-6-[1(R)-allyloxycarbonyloxyethyl]-1-methylcarbapen-2-em-3-carboxylate is reacted with the side chain (compound B) as set forth in the following Table to produce compounds of formula A.
TABLE
| Example # | B | |
|---|---|---|
| 8 | | |
| 9 | | |

TABLE-continued

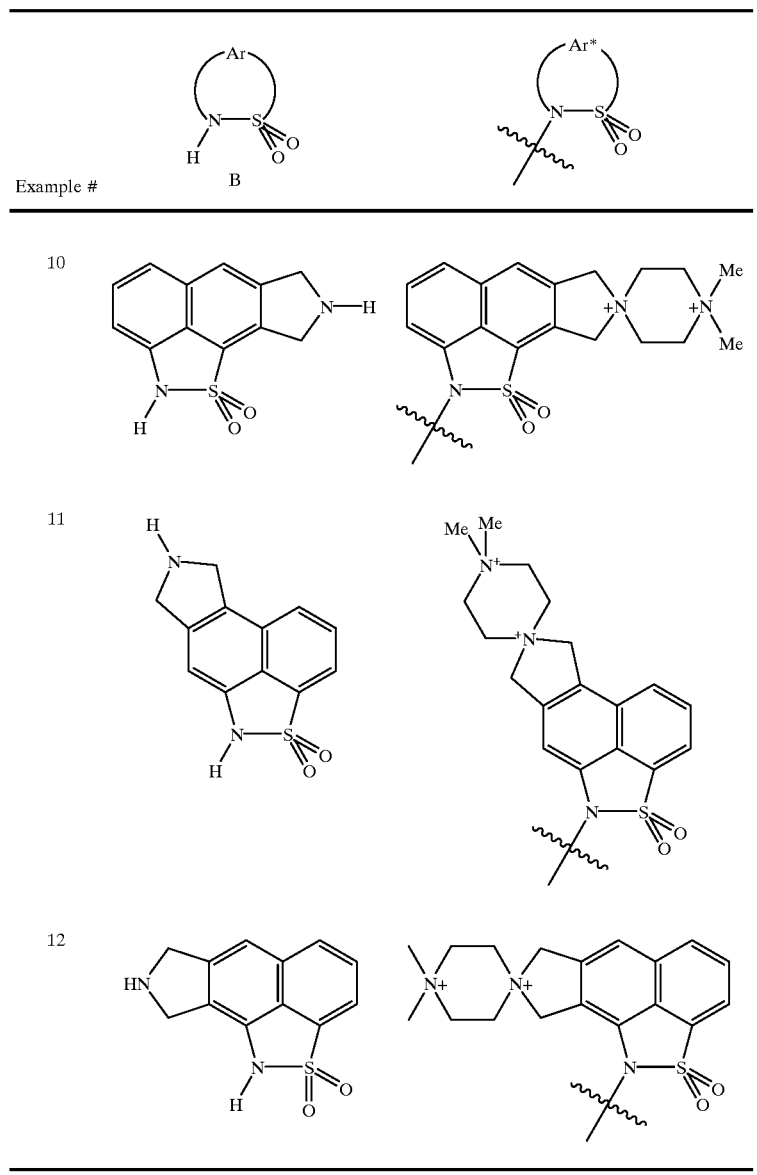

What is claimed:
1. A compound of formula I:

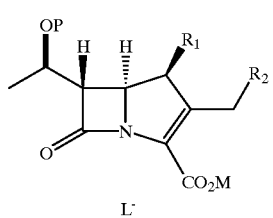

or a pharmaceutically acceptable salt thereof, wherein:
CO₂M represents a carboxylic acid or a carboxylate anion;
L⁻ represents a counterion, present as necessary to balance a quaternary nitrogen cation;
$R^1$ represents H or methyl;
P represents hydrogen, hydroxyl, or F;
$R^2$ represents:

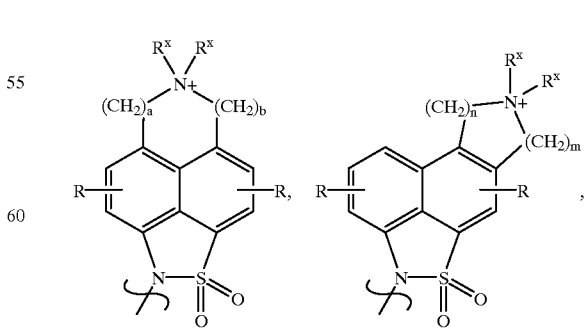

a = 0 to 3; b = 0 to 3
such that a + b = 1 to 3 n = 0 to 4; m = 0 to 4
such that n + m = 2 to 4

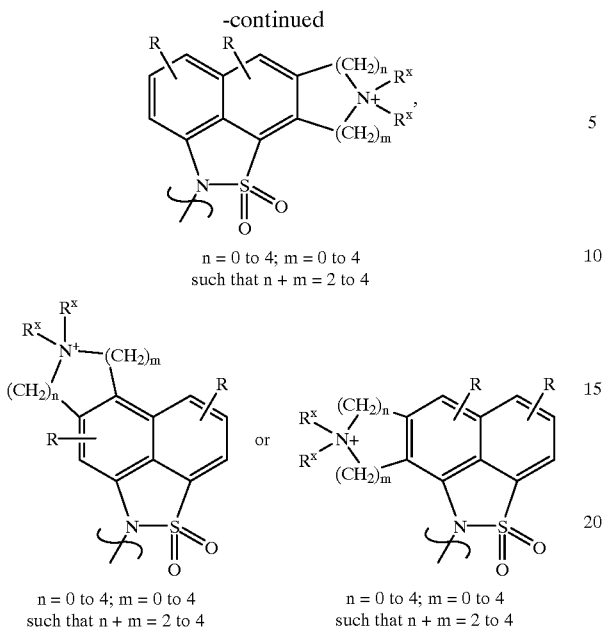

n = 0 to 4; m = 0 to 4
such that n + m = 2 to 4 n = 0 to 4; m = 0 to 4
such that n + m = 2 to 4 n = 0 to 4; m = 0 to 4
such that n + m = 2 to 4 wherein:

each R is independently selected from: —R*; hydrogen; halo; —CN; —NO$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^h$; —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{1-7}$ cycloalkyl, unsubstituted or substituted with one to four R$^d$ groups;

or R$^a$ and R$^b$ taken together with any intervening atoms represent a 4–6 membered saturated, heterocyclic ring consisting of the N of attachment and carbon atoms and optionally interrupted by one or more of O, S, NR$^c$, with R$^c$ as defined above, or —C(O)—, said ring being unsubstituted or substituted with one to four R$^i$ groups;

or R$^b$ and R$^c$ taken together with any intervening atoms represent a 4–6 membered heterocyclic ring consisting of the N of attachment and carbon atoms and optionally interrupted by one to three of O, S, NR$^a$, with R$^a$ as defined above, or —C(O)—, said ring being unsubstituted or substituted with one to four R$^i$ groups;

each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$CONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —R*;

R$^e$, R$^f$ and R$^g$ represent hydrogen; —R*; —C$_{1-6}$ straight- or branched-chain alkyl unsubstituted or substituted with one to four R$^i$ groups;

or R$^e$ and R$^f$ taken together with any intervening atoms represent a 4–6 membered saturated ring consisting of the N of attachment and carbon atoms and optionally interrupted by one to three of O, S, —C(O)— or NR$^g$ with R$^g$ as defined above, said ring being unsubstituted or substituted with one to four R$^i$ groups;

each R$^i$ independently represents halo; C$_{1-6}$ straight or branched chain alkyl; —CN; —NO$_2$; phenyl; —NHSO$_2$R$^h$; —OR$^h$; —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

each R$^h$ independently represents hydrogen, —C$_{1-6}$ straight or branched-chain alkyl group, —C$_3$–C$_6$ cycloalkyl group or phenyl, or when two R$^h$ groups are present, said R$^h$ groups may be taken in combination and represent a 4–6 membered saturated ring, said saturated ring being optionally interrupted by one or two of O, S, SO$_2$, —C(O)—, NH and NCH$_3$;

R* is selected from the group consisting of:

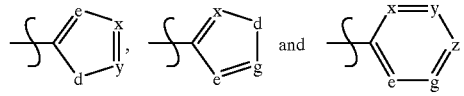

wherein:

d represents O, S or NR$^k$;

e, g, x, y and z represent CR$^m$, N or N$^+$R$^k$, provided that no more than one of e, g, x, y and z in any given structure represents N$^+$R$^k$;

R$^k$ represents hydrogen; —C$_{1-6}$ straight- or branched-chain alkyl, unsubstituted or substituted with one to four R$^i$ groups;

each R$^m$ independently represents a member selected from the group consisting of: hydrogen; halo; —CN; —NO$_2$; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$; —NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups;

R$^n$ and R$^o$ represent hydrogen, phenyl; —C$_{1-6}$ straight- or branched-chain alkyl unsubstituted or substituted with one to four R$^i$ groups;

each R$^w$ independently represents hydrogen; —C$_{1-6}$ straight- or branched-chain alkyl, C$_{3-6}$ cycloalkyl, said alkyl or cycloalkyl being optionally substituted with 1–4 R$^i$ groups; phenyl, or heteroaryl, said phenyl and heteroaryl being optionally substituted with 1–4 R$^i$ groups;

or R$^h$ and R$^w$ taken together with any intervening atoms represent a 5–6 membered saturated ring consisting of the N of attachment and carbon atoms and, optionally interrupted by one or two of O, S, SO$_2$, NH or NCH$_3$;

each R$^x$ independently represents hydrogen or a C$_{1-8}$ straight- or branched-chain alkyl, optionally interrupted by one or two of O, S, SO, SO$_2$, NR, N$^+$R$^h$R$^w$, or —C(O)—, said alkyl being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl or heteroaryl group, said phenyl or heteroaryl is in turn optionally substituted with from one to four R$^i$ groups or with one to two C$_{1-3}$ straight- or branched-chain alkyl groups, said alkyl groups being unsubstituted or substituted with one to four R$^i$ groups;

or two R$^x$ groups taken together with any intervening atoms represent a 4–6 membered saturated heterocyclic ring consisting of the N of attachment and carbon atoms and optionally interrupted by O, S, SO$_2$, NR$^w$, N$^+$R$^w$R$^w$ or —C(O)—, said saturated ring being unsubstituted or substituted with 1–4 R$^i$ groups, where R$^w$ and R$^i$ are defined above, or two R$^w$ groups taken together with any intervening atoms represent a 4–6 membered saturated, heterocyclic consisting of the N of attachment and carbon atoms and ring optionally interrupted by O, S, SO$_2$, NR$^h$, N$^+$R$^h$R$^h$ or —C(O)—, said saturated ring being unsubstituted or substituted with 1–4 R$^i$ groups, where R$^h$ and R$^i$ are defined above, with the proviso that no more than two cations are present in formula I.

2. A compound selected from the group consisting of the structural formulae:

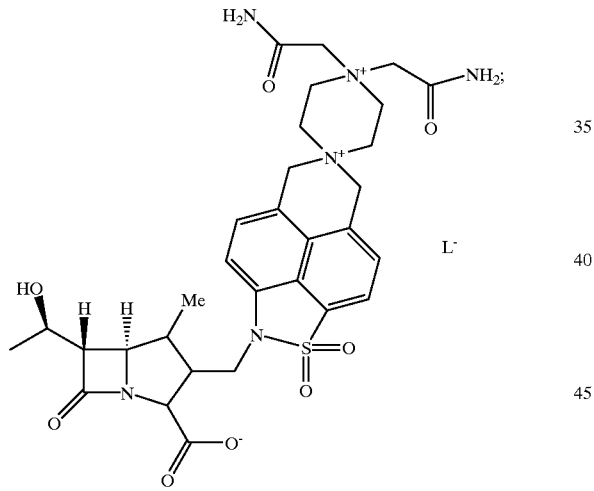

E-1

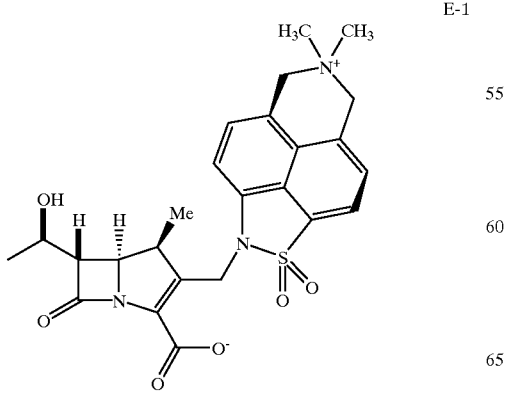

-continued

E-2

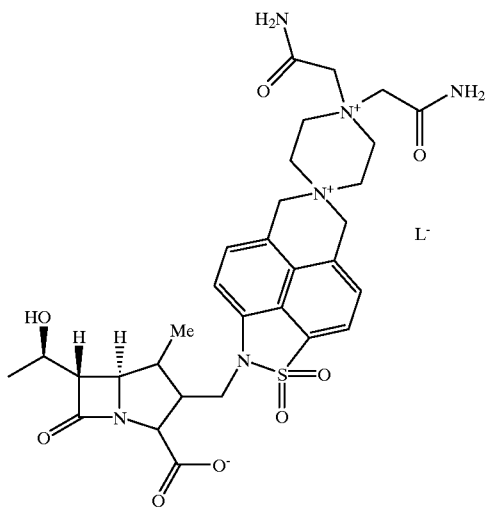

E-3

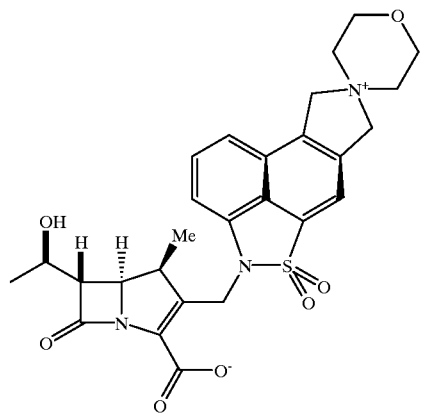

E-4

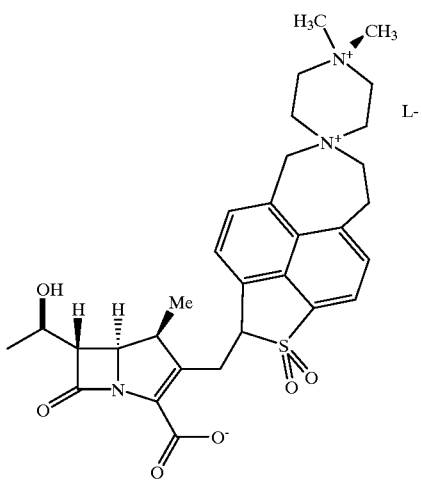

E-5
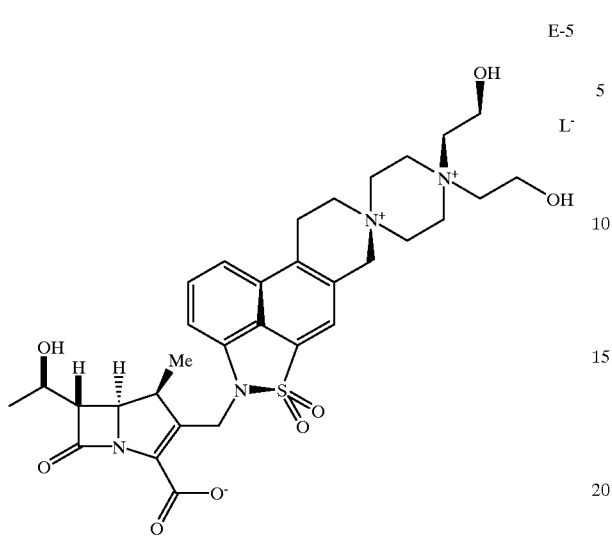
E-6
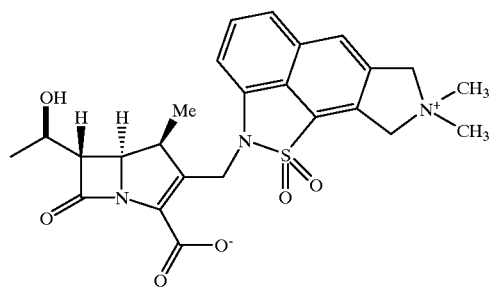
E-7
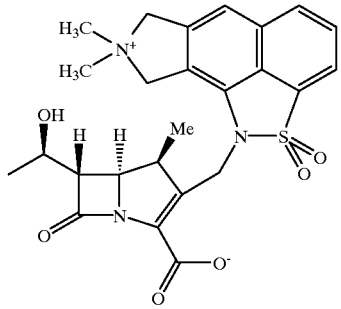
E-8
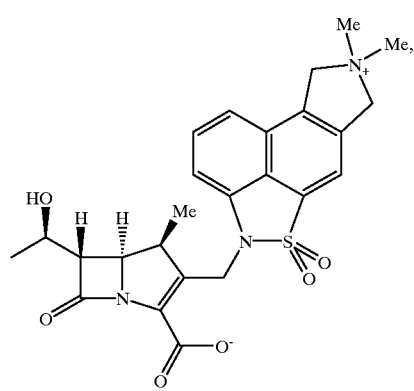
E-9
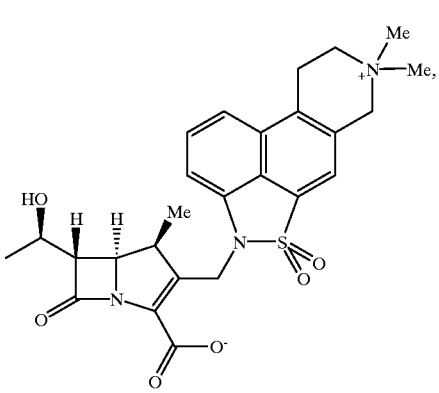
E-10
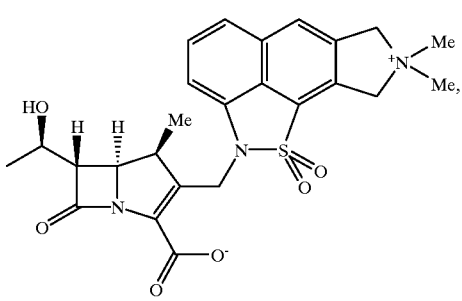
E-11
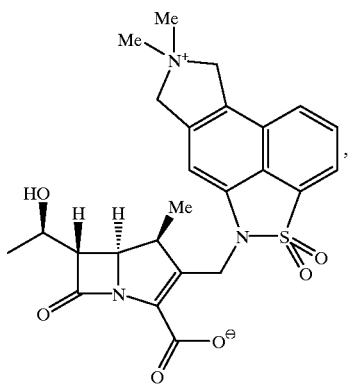
E-12
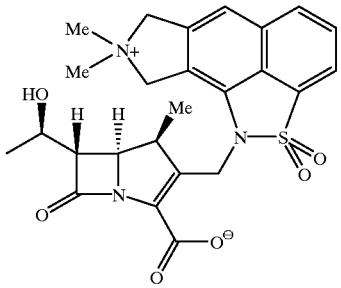

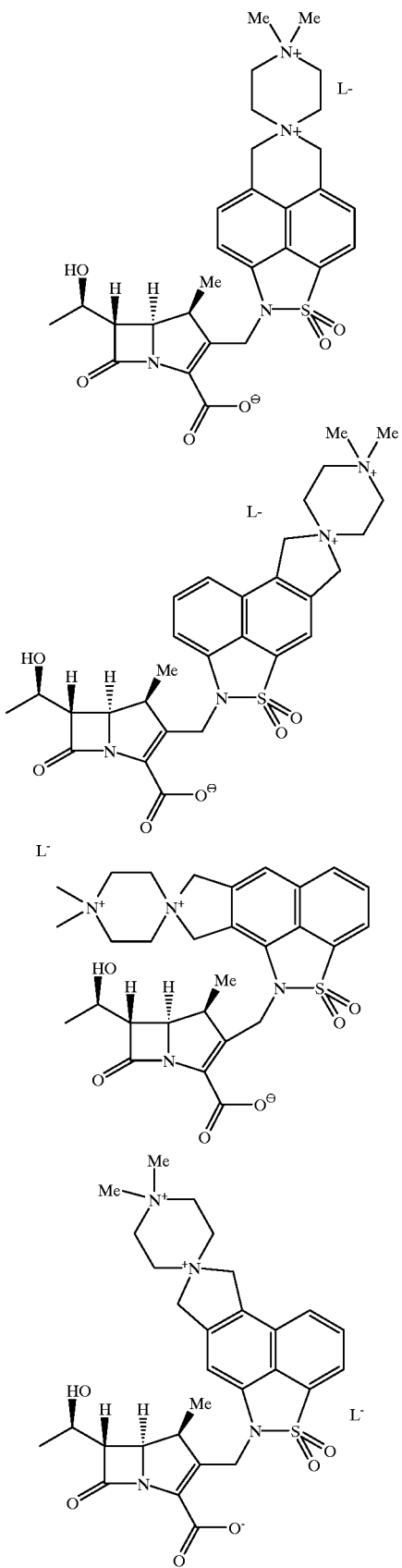

wherein L⁻ represents a pharmaceutically acceptable counterion.

3. A compound in accordance with claim 1 wherein:

one R* group is present and is selected from:

d represents $NR^k$; $R^k$ represents —$C_{1-6}$ straight or branched chain alkyl; and e, g, x and y represent $CR^m$ or $N^+R^k$, with $R^m$ representing hydrogen and all other variables as originally described.

4. A compound in accordance with claim 1 wherein $R^x$ represents hydrogen or a $C_{1-8}$ straight- or branched-chain alkyl or two $R^x$ groups taken together with any intervening atoms represent a 4–6 membered saturated ring optionally interrupted by O, S, $SO_2$, $NR^w$, $N^+R^wR^w$ or —C(O)—, said alkyl or saturated ring being unsubstituted or substituted with 1–4 $R^i$ groups.

5. A compound in accordance with claim 4 wherein the saturated ring is interrupted by $N^+R^wR^w$.

6. A compound in accordance with claim 1 wherein one R group represents a H, —$C_{1-6}$ straight or branched chain alkyl group, substituted with one to four $R^d$ groups, wherein one $R^d$ group represents —R*.

7. A compound in accordance with claim 1 represented by formula Ia:

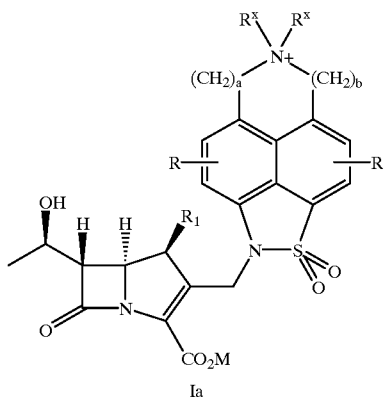

Ia or a pharmaceutically acceptable salt thereof, wherein:
a=0 to 3 and b=0 to 3 such that a+b=1 to 3.

8. A compound according to claim 7 wherein:
a=1 to 2 and b=1 to 2 such that a+b=2 to 3;
$CO_2M$ represents a carboxylate anion; and
$R^1$ represents methyl.

9. A compound according to claim 7 wherein:
a=1 to 2 and b=1 to 2 such that a+b=2 to 3;
$CO_2M$ represents a carboxylate anion;
$R^1$ represents methyl;
each R represents hydrogen;
$R^h$ represents hydrogen or $C_{1-6}$ straight or branched chain alkyl group;
and all other variables as originally defined.

10. A compound according to claim 1 represented by formula Ib:

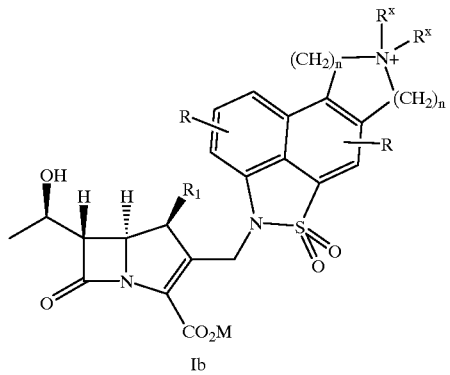

Ib or a pharmaceutically acceptable salt thereof, wherein:
n=0 to 4 and m=0 to 4 such that n+m=2 to 4;
and all other variables are as originally defined.

11. A compound according to claim 10 wherein:
n=1 to 2 and m=1 to 2 such that n+m=2 to 4;
$CO_2M$ represents a carboxylate anion;
$R^1$ represents methyl;
and all other variables are as originally defined.

12. A compound according to claim 10 wherein:
n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;
and all other variables as originally defined.

13. A compound according to claim 1 represented by formula Ic:

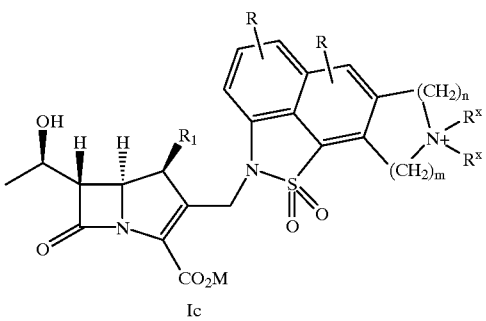

Ic or a pharmaceutically acceptable salt thereof, wherein:
n=0 to 4 and m=0 to 4 such that n+m=2 to 4;
and all other variables are as orginally described.

14. A compound according to claim 13 wherein:
n=1 to 2 and m=1 to 2 such that n+m=2 to 4;
$CO_2M$ represents a carboxylate anion;
$R^1$ represents methyl;
and all other variables are as described above.

15. A compound according to claim 13 wherein:
n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;
and all other variables are as originally defined.

16. A compound according to claim 1 represented by formula Id:

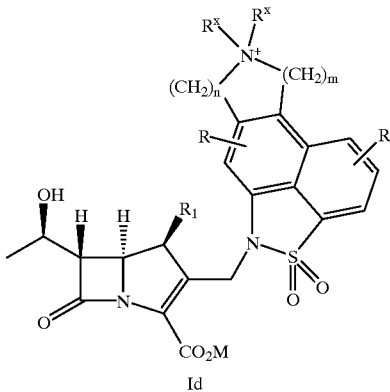

Id or a pharmaceutically acceptable salt thereof, wherein:
n=0 to 4 and m=0 to 4 such that n+m=2 to 4;
and all other variables are as originally described.

17. A compound according to claim 16 wherein:
n=1 to 2 and m=1 to 2 such that n+m=2 to 4;
$CO_2M$ represents a carboxylate anion;
$R^1$ represents methyl;
and all other variables are as originally described.

18. A compound according to claim 16 wherein:
n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;
and all other variables as originally defined.

19. A compound according to claim 1 represented by formula Ie:

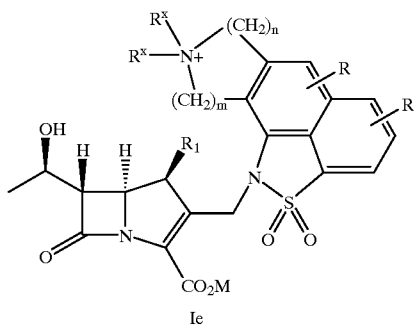

Ie or a pharmaceutically acceptable salt thereof, wherein:
n=0 to 4 and m=0 to 4 such that n+m=2 to 4;
and all other variables are as described above.

20. A compound according to claim 19 wherein:
n=1 to 2 and m=1 to 2 such that n+m=2 to 4;
$CO_2M$ represents a carboxylate anion;
$R^1$ represents methyl;
and all other variables are as described above.

21. A compound according to claim 19 wherein:
n=1 to 2 and m=1 to 2 such that n+m=2 to 4;
$CO_2M$ represents a carboxylate anion;
$R^1$ represents methyl;
each R represents hydrogen;
$R^h$ represents hydrogen or $C_{1-6}$ straight or branched chain alkyl group;
and all other variables are as originally defined.

22. A method of treating or preventing bacterial infection in a mammalian patient in need thereof, comprising administering to said patient an effective amount of a compound of claim 1.

23. A pharmaceutical composition comprised of a compound in accordance with claim 1 in combination with a pharmaceutically acceptable carrier.

* * * * *